United States Patent

Doiron et al.

[11] Patent Number: 5,267,995
[45] Date of Patent: Dec. 7, 1993

[54] OPTICAL WAVEGUIDE WITH FLEXIBLE TIP

[75] Inventors: Daniel R. Doiron, Santa Ynez; Hugh L. Narciso, Jr., Santa Barbara, both of Calif.

[73] Assignee: PDT Systems, Santa Barbara, Calif.

[21] Appl. No.: 938,707

[22] Filed: Sep. 1, 1992

[51] Int. Cl.⁵ ............................................. A61B 17/32
[52] U.S. Cl. ...................................... 606/15; 385/123
[58] Field of Search .................. 606/7, 14, 15, 16, 17; 385/123

[56] References Cited

U.S. PATENT DOCUMENTS

| | | | |
|---|---|---|---|
| 4,273,109 | 6/1981 | Enderby | 606/15 |
| 4,630,890 | 12/1986 | Ashkin et al. | 385/123 |
| 4,660,925 | 4/1987 | McCaughan, Jr. | 606/15 |
| 4,676,594 | 6/1987 | Presby | 385/123 |
| 4,678,273 | 7/1987 | Vilhelmsson | 385/123 |
| 5,104,392 | 4/1992 | Kittrell et al. | 606/7 |
| 5,139,494 | 8/1992 | Freiberg | 606/16 |

Primary Examiner—Stephen C. Pellegrino
Assistant Examiner—Sonya Harris
Attorney, Agent, or Firm—Michael G. Petit

[57] ABSTRACT

A flexible tip for a medical catheter suitable for the transmission of light and dimensioned to pass through extremely small tubular members is described. The flexible tip, preferably made of optically transparent silicone elastomer, is affixed to the terminal end of a conventional optical fiber. In a preferred embodiment, the flexible tip comprises a central silicone core surrounded by a cladding having an index of refraction less than that of the core, permitting internal reflection. The flexible tip is provided with an outer jacket which serves two purposes: a) it provides structural integrity for the tip, and b) it reinforces the union between the flexible tip and the optical fiber to which it is abutted. The tip enables the delivery of a comparable amount of light as a large glass fiber of equal core diameter but possesses much greater flexibility. The tip has the flexibility to be able to enter tortuous tubular members while retaining the light transmitting capabilities of relatively inflexible glass optical waveguides of the same diameter.

10 Claims, 3 Drawing Sheets

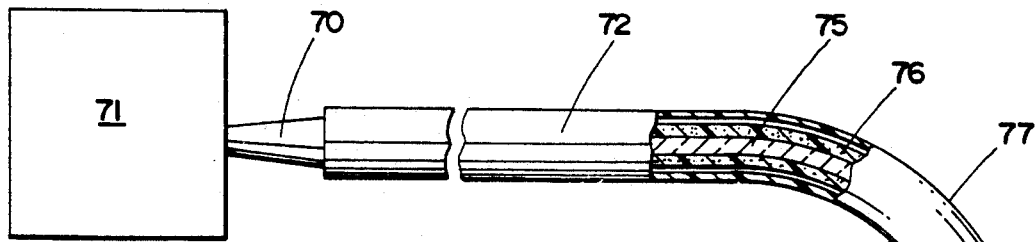
*Fig. 7*
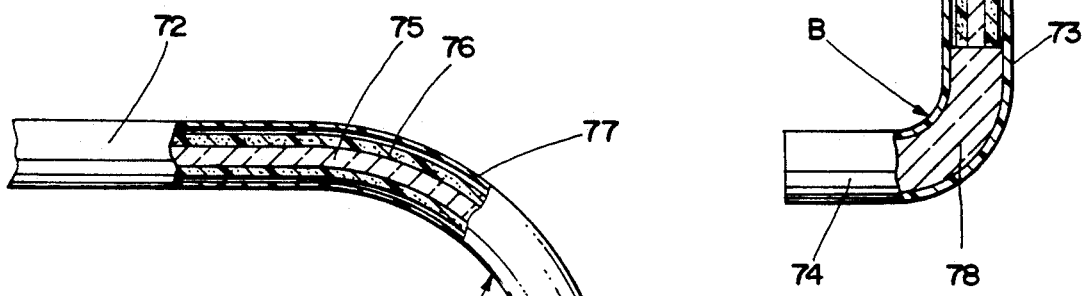
*Fig. 8(a)*
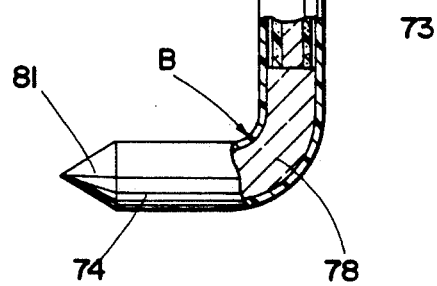
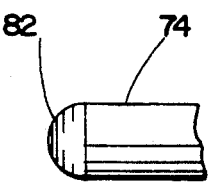
*Fig. 8(b)*   *Fig. 8(c)*

OPTICAL WAVEGUIDE WITH FLEXIBLE TIP

BACKGROUND OF THE INVENTION

1. Field of the Invention

The invention relates generally to the field of interventional optical catheters and, more specifically, to a flexible terminus or tip for transluminal surgical catheters and the like.

2. Prior Art

The use of energy delivered from a light source, for example, a laser, for surgical and industrial applications is well documented. Typically, optical waveguides such as silica optical fibers (alternatively referred to herein as "fiber optics") are used to deliver light energy to internal areas of the human body not readily accessed directly by the light source. A growing number of procedures, such as laparoscopic cholecystectomy, laparoscopic appendectomy, lithotripsy of calculi of the biliary, salivary and urinary tracts, and a host of other light energy surgeries require flexible fiber optics to access and deliver substantial energy to the treatment sight.

Often, fiber optics which are flexible enough to access deep, tortuous internal areas of the body are so small in diameter that they lack the rigidity required to push them through the lumen and/or excessive energy density in the fiber causes damage to the fiber rendering such thin fiber optics impractical. Moreover, transmitting higher powers, on the order of 10 or more watts, is inefficient in small fibers due to the difficulty of coupling. Energy density at the fiber optic tip is the total energy delivered divided by the cross sectional area of the optical fiber.

High energy densities cause undesired damage to the tip of the fiber. The solution to this problem, with present technology, is either using larger core diameter optical fibers, which while reducing the energy density, substantially reduces the flexibility (doubling the core size reduces the flexibility fourfold), or using a bundle of small core diameter fiber optics creating a large proportion of dead space. Dead space, as used herein, refers to the portion of the cross sectional area of a fiber optic catheter which does not transmit light energy.

Large core fiber optics permit the relatively efficient coupling of energy from an external source into the fiber; even if the source is divergent. This is not true of small core fibers. The coupling efficiency of large cores together with their rigidity enables them to be readily advanced through a straight lumen and conduct a large amount of light energy to the tip. The disadvantage is that the tip lacks the flexibility to follow a tortuous path.

With conventional laser catheter tips heat buildup is a significant problem. Sapphire or another expensive heat-stable material is frequently used at the tip of such catheters to prevent heat-induced fracturing and subsequent disintegration. Laser surgery is conveniently done by using a flexible quartz fiber for transmitting the laser energy, usually from a Nd:YAG laser source, to the tissue undergoing treatment. In a typical laser surgery system the end or tip of the silica fiber optic serves as the probe for radiating the tissue to effect incision or coagulation thereof. With some fiber optic tips it is desirable to hold the tip away from direct contact with the tissue to avoid fouling of the fiber and, importantly, to avoid heat damage to the fiber end. Noncontact laser systems employing a light transmitting member at the output end of the fiber to focus or otherwise alter the radiation characteristics of the fiber have also been proposed, for example, by Enderly in U.S. Pat. No. 4,273,109, and by Daikuzono in U.S. Pat. No. 4,736,743. Microlenses may also be employed to distribute the light exiting the catheter. The problem with the foregoing termini for laser catheters is that they lack the flexibility to enter small tortuous tubular members such as blood vessels, vas deferens, ureters and so forth.

SUMMARY OF THE INVENTION

It is an object of this invention to provide a minimally invasive medical, light transmitting catheter having the light transmitting capability of a large core conventional silica fiber dimensioned to fit within very small tubular members but having much greater flexibility at the distal end that a comparable silica fiber optic.

It is yet another object of this invention to provide a tip having substantially the same light transmitting capabilities as silica tips having a much larger diameter while exhibiting greater flexibility at the tip than can be achieved with silica.

It is still another object of this invention to provide a transluminal catheter for conducting light from a source to a distal target which has the advantages of a large core silica fiber for coupling light from a source into the fiber and permitting advancement of the catheter through the lumen and having a tip which has the flexibility of a small core silica fiber.

It is yet another object of this invention to provide a flexible tip for a medical light delivery catheter of a composition amenable to being formed in many different geometries or configurations.

These and other objects of the invention will soon become apparent as we turn now to the descriptions of the preferred embodiment.

BRIEF DESCRIPTION OF THE DRAWINGS

FIG. 7 is a partially cutaway schematic view of an embodiment of the invention used with a divergent light source.

FIG. 8 shows the embodiment of FIG. 7 with the flexible tip fitted with a terminus configured as (a) a pointed probe, (b) a rounded smooth terminus, and (c) a focusing lens.

DESCRIPTION OF THE PREFERRED EMBODIMENT

Figure 1:
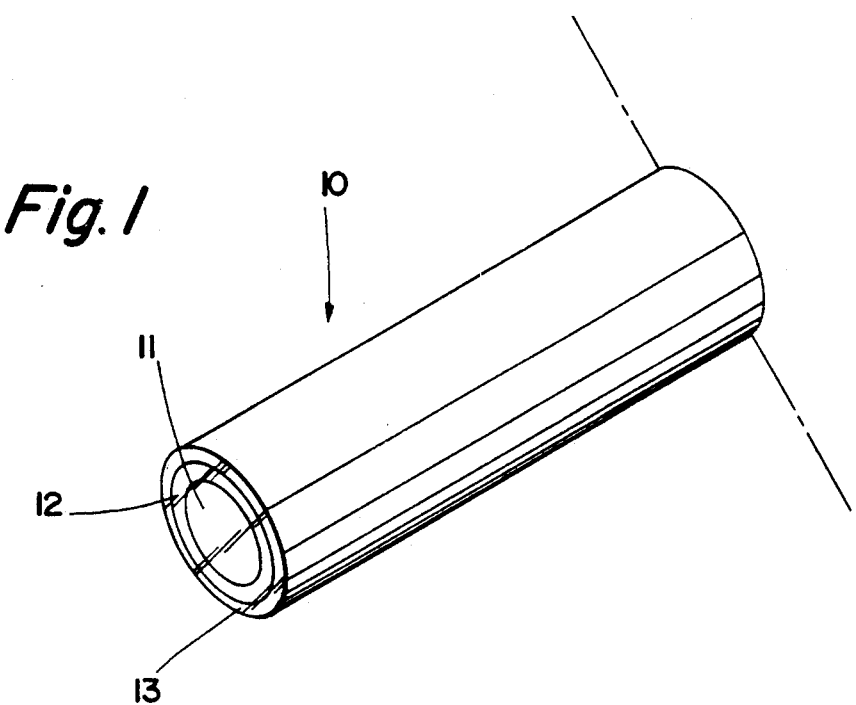
FIG. 1 is a perspective view of the tip of the catheter of the present invention.

A flexible tip for use with the invasive catheter of the present invention is shown in FIG. 1, generally indicated at 10. The central core 11 of the flexible tip 10 is made from an optically transmissive material such as silicone, silicone copolymer, or any variety of elastomers. Surrounding the central core 11 is a cladding layer 12, again fabricated from silicone, silicone copolymer or elastomer. The cladding layer 12 and the core 11 are specifically chosen for their refractive indices. The refractive index of the cladding 12, which may be a length of tubing, is preferably less than the refractive index of the core 11. Correctly choosing the refractive indices of the materials will insure total internal reflection of the light energy while also controlling the solid angle of the exiting light energy (not shown). The tip 10 shown in FIG. 1 is abutted to a single fiber (not shown) or fiber bundle (not shown) to receive the light from the optical fiber(s) (not shown) and ultimately to deliver the light energy to the treatment site. The tip core 11 and the cladding 12 are held in position relative to the fiber optic (not shown) by a structural tube 13 made with flexible elastomeric material such as Teflon TM or polyurethane.

Figure 2:
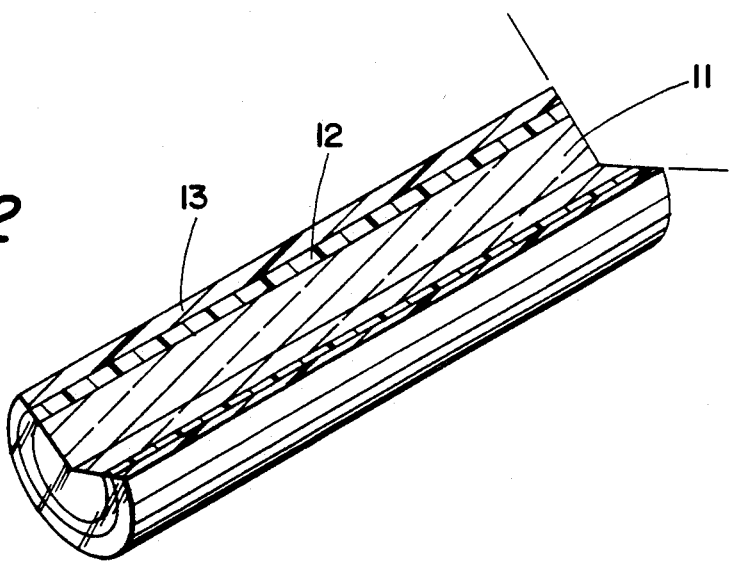
FIG. 2 is a partially cutaway view of the tip of FIG. 1.
Figure 3:
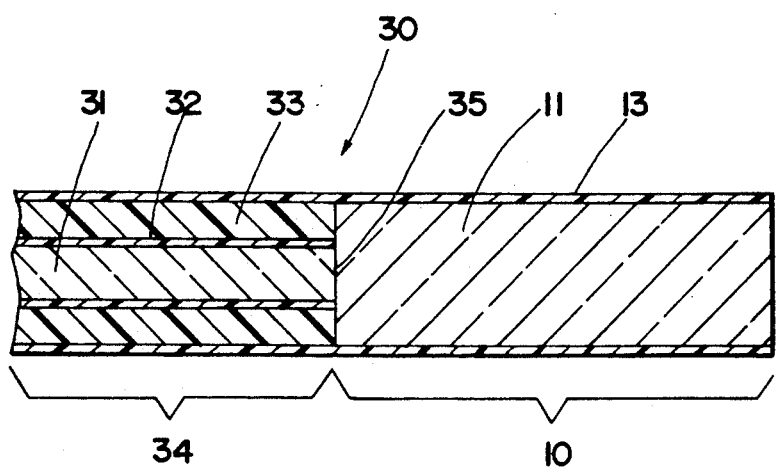
FIG. 3 is a longitudinal cutaway view of the catheter of the present invention with a first preferred embodiment of the tip in place.
Figure 4:
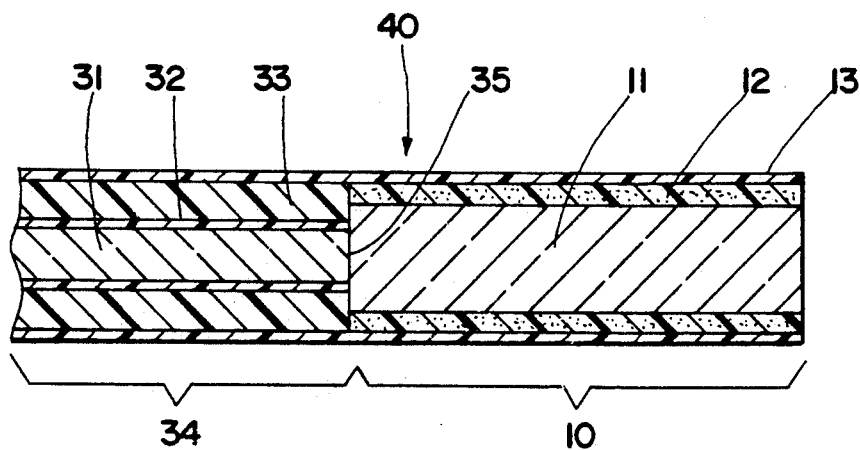
FIG. 4 is a longitudinal cutaway view of the catheter of the present invention with a second preferred embodiment of the diffuser tip in place.

FIG. 2 is a cut away view of the tip of FIG. 1. It is clear that the optically transmissive tip core 11 is surrounded by a cladding layer 12 which in turn is surrounded by a structural tube 13 made of flexible elastomeric material. The outer tube 13 may, of course, be made from a variety of flexible elastomers including Teflon TM and polyethylene. The catheter of the present invention, showing the flexible tip abutted to the terminus of the fiber optic is shown in FIG. 3. The catheter, generally indicated at numeral 30, has a fiber optic portion 34 abutted to the flexible tip portion 10. The fiber optic portion 34 of the catheter 30 comprises a fiber central core 31 surrounded by a cladding 32. The core 31 and cladding 32 are enclosed in a jacket 33. The distal tip, or terminus, 35 of the optical fiber portion 34 is abutted against the tip core 11 of the flexible tip 10. The tip core 11 is surrounded by tip an outer sheath 13. Treatment light (not shown) exits the tip of the catheter 30 in FIG. 3 in the forward direction towards the right. The flexible tip 10 may also include a cladding 12 surrounding the tip core 11 as shown in embodiment 40 in FIG. 4.

Figure 5:
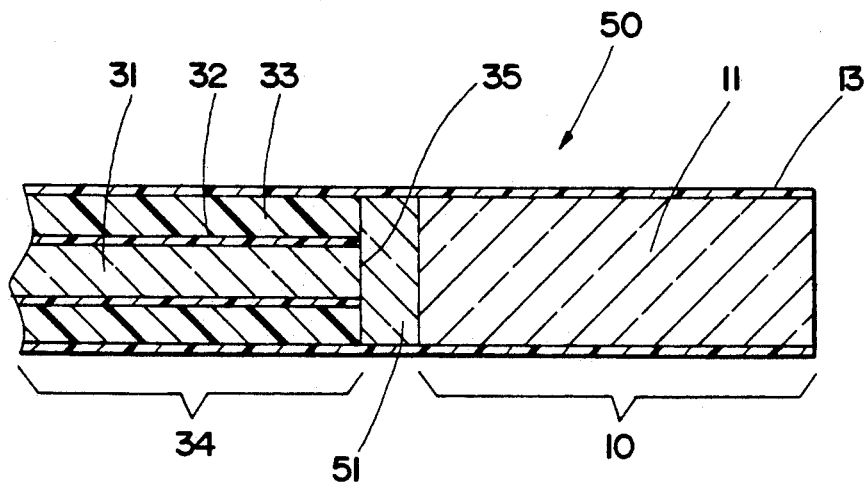
FIG. 5 is another longitudinal, cross sectional view of an embodiment of the catheter of the current invention with the core of the flexible tip spaced from the core of the optical fiber.

A second preferred embodiment of the catheter of the present is generally indicated at 50 in FIG. 5. In this embodiment the distal tip 35 of the optical fiber portion 34 is spaced from the flexible tip core 11 of the tip portion 10 by means of a liquid or gas-filled space 51. The fluid gap 51 allows greater power handling capabilities by substantially reducing the power density of the transmissive core 11/fluid gap 51 interface compared to the transmissive core 11/fiber optic 31 interface. The fluid space 51 may be filled with a gas or a fluid.

Figure 6:
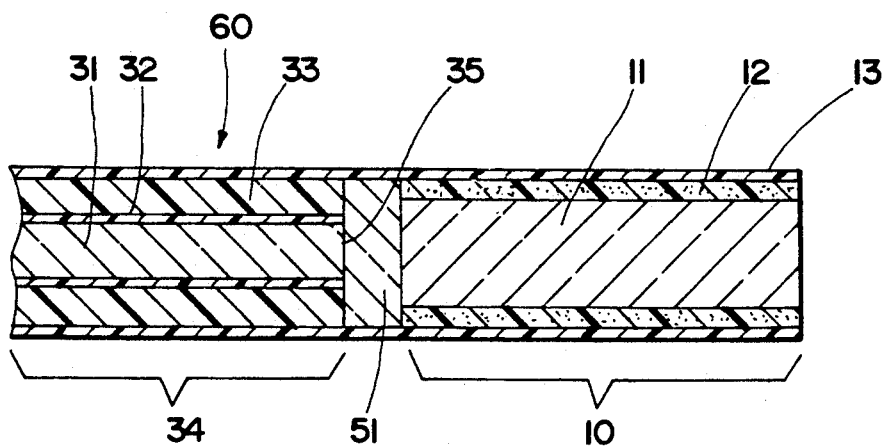
FIG. 6 is the same as FIG. 5 except a cladding surrounds the core material of the tip.

FIG. 6 shows yet another embodiment 60 of the catheter shown in FIG. 5 except that the flexible tip has a cladding material 12 surrounding the flexible tip core 11 of the flexible tip 10.

It is important that the fiber optic core 31 retain its cladding 32 during fabrication of the catheter. If the cladding 32 is stripped from around the core 31 of the fiber optic 34, the catheter will be vulnerable to breakage at the point where the cladding has been stripped from the core. The material chosen for the fiber optic core is less elastic of flexible than the material chosen for the core of the flexible tip.

The advantage of combining a large core silica fiber with an elastomer tip is seen by looking now to FIG. 7. Divergent light 70 from a divergent source such as a diode laser 71 readily enters the large core 75 of the silica fiber 72 which conducts the light to the core 78 of the flexible elastomeric tip 74. Optically transparent silicone rubber is preferably employed as a material of choice for the tip 74 due to its biocombatibility. The index of refraction of the material comprising the flexible tip 74 is preferably close to that of the core 75 of the fiber optic. Alternatively, the space 51 in the embodiment shown in FIGS. 5 and 6 may be filled with a optically transparent material having an index of refraction between the index of the tip core 74 and the fiber core 75. The relative stiffness of the large diameter silica core 75, enhanced by the presence of cladding jacket 76 and outer sheath 77, permits advancement of the catheter through constricted tubular tissue but has a large minimum radius of curvature A. The silicone core tip 74, being relatively short compared to the silica core fiber optic 72 portion, is pushed ahead of the fiber portion 72 during advancement. The silicone core tip, being more flexible, has a much smaller minimum radius curvature, shown at B in FIG. 7, enabling it to track sharp turns, guiding the silicone core portion 72 during advancement. The silicone core tip 74 and the silica core 75 of the fiber optic portion 72 of the waveguide form a high coupling efficiency union 73. This union 73 can conveniently be made by extending the sheath (not shown) surround the silica core portion beyond the silica core portion and filling the sheath with uncured silicone followed by curing.

FIG. 8 shows the embodiment of the flexible tipped waveguide of FIG. 7 with a variety of flexible tip terminus configurations. Since the flexible tip 74 is elastomeric, it readily bonds to various other plastics. FIG. 8(a) shows the flexible tip 74 with a pointed terminus 81 suitable for interstitial use. A rounded or beveled terminus 82 (FIG. 8(b) is useful for intraluminal use. FIG. 8(c) shows a focusing lens 83 affixed to the flexible tip 74. The termini 81-83 may be fabricated from any transparent material or they may be opaque if the light reaching the flexible tip 74 tip need not exit the tip in the forward direction.

It will be appreciated that, while a preferred embodiment of the invention has been described herein, various modifications will suggest themselves to those skilled in the art. For example, variations in materials may be required for certain industrial applications. The essential feature of the invention is the placement of a flexible tip on a relatively rigid, large core optical fiber to confer the advantages of both materials to a combination product while minimizing their disadvantages. Rigid, large core fibers having relatively inflexible cores comprising a transparent material other than silica such as a plastic may be used. Flexible elastomers other than silicone may also be used for the tip. These and other modifications that may suggest themselves to those skilled in the art are considered to be within the spirit and scope of the present invention as set forth in the following claims.

What I claim is:

1. A medical catheter for conveying light energy from a source of said light energy to a tissue undergoing light treatment, the catheter comprising:

(a) a fiber optic portion having a first proximal and a first distal end and a light-transmitting first core having a first flexibility coextensive with said fiber optic portion; and (b) a tip portion, located at said first distal end said tip portion comprising a light-transmitting second core having a second proximal and second distal end, said second core consisting of a light-transmitting elastomer having a second flexibility greater than said first flexibility, the second proximal end of said second core being in optical communication with said first distal end of said first core, and wherein said second proximal end of said tip portion is affixed to said first distal end of said optical fiber portion of said catheter.

2. The medical catheter of claim 1 further comprising an outer sheath surrounding said second core.

3. The medical catheter of claim 2 further comprising a layer of cladding interposed between said second core and said outer sheath.

4. The medical catheter of claim 3 wherein said cladding consists of silicone elastomer.

5. The medical catheter of claim 1 wherein said elastomer comprises optically transparent silicone.

6. The medical catheter of claim 1 further comprising a point terminus affixed to said second distal end of said tip portion.

7. The medical catheter of claim 1 further comprising a rounded terminus affixed to said second distal end of said tip portion.

8. The medical catheter of claim 1 further comprising a focusing lens affixed to said second distal end of said tip portion.

9. A medical catheter for conveying light energy from a source of said light energy to a tissue undergoing light treatment, the catheter comprising:
 (a) a fiber optic portion having a first proximal and first distal end and a light transmitting first core coextensive with said fiber optic portion; and
 (b) a tip portion located at said first distal end comprising alight-transmitting second core, said second core consisting of a light-transmitting elastomer, said second core having a second proximal and second distal end, said second proximal end o said second core being in optical communication with at least a portion of said first distal end, and wherein a space is interposed between said second proximal end of said tip portion and the first distal end of said optical fiber portion of said catheter.

10. The medical catheter of claim 1 or claim 9 wherein said first core has a first index of refraction and said second core has a second index of refraction and wherein said space is filled with a light-transmitting material, said light-transmitting material having a third index of refraction, said third index of refraction being intermediate to said first index of refraction and said second index of refraction.

* * * * *